United States Patent

Nighan, Jr. et al.

[11] Patent Number: 5,991,317
[45] Date of Patent: Nov. 23, 1999

[54] RETINAL PHOTOCOAGULATOR INCLUDING DIODE PUMPED, MULTI-AXIAL MODE INTRACAVITY DOUBLED LASER

[75] Inventors: William L. Nighan, Jr., Menlo Park; John Cole, Sunnyvale, both of Calif.

[73] Assignee: Spectra Physics Lasers, Inc., Mountain View, Calif.

[21] Appl. No.: 09/035,680

[22] Filed: Mar. 5, 1998

Related U.S. Application Data

[63] Continuation of application No. 08/446,203, May 19, 1995, which is a continuation-in-part of application No. 08/191,656, Feb. 4, 1994, Pat. No. 5,446,749.

[51] Int. Cl.⁶ ........................................................ H01S 3/10
[52] U.S. Cl. .................................... 372/22; 372/108
[58] Field of Search ................. 372/22, 108; 600/168, 600/181

[56] References Cited

U.S. PATENT DOCUMENTS

| | | |
|---|---|---|
| 3,720,213 | 3/1973 | Hobart et al. . |
| 4,309,998 | 1/1982 | Aron nee Rosa et al. . |
| 4,656,635 | 4/1987 | Baer et al. . |
| 4,701,929 | 10/1987 | Baer et al. . |
| 4,809,291 | 2/1989 | Byer et al. ............................ 372/75 |
| 4,884,277 | 11/1989 | Anthon et al. . |
| 4,951,294 | 8/1990 | Basu et al. . |
| 5,052,815 | 10/1991 | Nightingale et al. . |
| 5,127,068 | 6/1992 | Baer et al. . |
| 5,136,597 | 8/1992 | Nightingale . |
| 5,151,909 | 9/1992 | Davenport et al. . |
| 5,164,947 | 11/1992 | Lukas et al. . |
| 5,170,409 | 12/1992 | Nightingale et al. . |
| 5,181,214 | 1/1993 | Berger et al. ............................ 372/34 |
| 5,253,260 | 10/1993 | Palombo ................................. 372/34 |
| 5,267,252 | 11/1993 | Amano .................................... 372/34 |
| 5,278,852 | 1/1994 | Wu et al. . |
| 5,377,212 | 12/1994 | Tatsuno et al. ......................... 372/22 |
| 5,548,604 | 8/1996 | Toepel ..................................... 372/35 |
| 5,638,388 | 6/1997 | Nighan, Jr. et al. ..................... 372/22 |

FOREIGN PATENT DOCUMENTS

| | | |
|---|---|---|
| 0 492 778 A1 | 10/1991 | European Pat. Off. . |
| 0 556 582 A1 | 1/1993 | European Pat. Off. . |

OTHER PUBLICATIONS

Baer, T., "Large–amplitude fluntuations due to longitudinal mode coupling in diode–pumped intracavity–doubled Nd:YAG lasers", *Journal of the Optical Society of America*, vol. 3, No. 9, pp. 1175–1179, Sep. 1986.

(List continued on next page.)

*Primary Examiner*—Rodney Bovernick
*Assistant Examiner*—Robert E. Wise
*Attorney, Agent, or Firm*—Wilson Sonsini Goodrich & Rosati

[57] ABSTRACT

A diode pumped, multi axial mode, intracavity doubled, intracavity tripled laser, includes at least two resonator mirrors defining a resonator cavity. A laser crystal and a doubling crystal are positioned in the resonator cavity. A tripling crystal is also positioned in the resonator cavity. A diode pump source supplies a pump beam to the laser crystal and produces a laser crystal beam with a plurality of axial modes that are incident on the doubling crystal. This produces a frequency doubled output beam.

Further, a diode pumped, multi axial mode, intracavity nonlinearly-converted laser is provided and includes at least two resonator mirrors defining a resonator cavity, a laser crystal and a nonlinear conversion apparatus positioned in the resonator cavity. A nonlinear conversion apparatus is also positioned in the resonator cavity. A diode pump source supplying a pump beam to the laser crystal and produces a laser crystal beam with a plurality of axial modes that are incident on the nonlinear conversion apparatus. The result is a nonlinearly converted output beam that has a % RMS noise of less than 3%.

7 Claims, 8 Drawing Sheets

OTHER PUBLICATIONS

James et al., "Elimination of chaos in an intracavity–doubled Nd:YAG laser", *Optics Letters*, vol. 15, No. 20, pp. 1141–1143, Oct. 15, 1990.

Magni et al., "Intracavity frequency doubling of a cw high–power $TEM_{00}$ Nd:YLF laser", *Optics Letters*, vol. 18, No. 24, pp. 2111–2113, Dec. 15, 1993.

Marshall et al., "Intracavity Doubled mode–locked and CW Diode–Pumped Lasers", *IEEE J. of Quantum Electronics*, vol. 28, No. 4, pp. 1158–1163, Apr. 1992.

Nightingale et al., "0.6W, Stable, Single Frequency, Green Laser", 1994 Compact Blue Green Laser Conference, paper PD6. No month.

Oka et al., "Stable intracavity doubling of orthogonal linearly polarized modes in diode–pumped Nd:YAG lasers", *Optics Letters*, vol. 13, No. 10, pp. 805–807, Oct. 1988.

Wiechmann et al. "Efficient Intracavity–Doubled Laser Diode Pumped Nd:SFAP Green Laser", paper TuD4, 1995 Advanced Solid State laser Conference. No month.

Wiechmann et al. "Efficient 1 Watt single Frequency Continuous Wave Green Generation from an Intracavity–Doubled Diode Pumped Nd:YVO4 Laser", papers TuD4 and WD4, 1995 Advanced Solid State laser Conference.

Magni, V., et al., "Intracavity Frequency Doubling of a CW High–Power TEM Nd:YLF Laser", *Optics Letters*, pp. 2111–2113, Dec. 1993.

Baer, T., "Large–Amplitude Fluctuations due to Longitudinal Mode Coupling in Diode–Pumped Intracavity–doubled Nd:YAG Lasers", Journal of the Optical Society of America B , pp. 1175–1180, Sep. 1986.

MUTI-AXIAL MODE, INTRACAVITY DOUBLED LASER USED AS PUMPER FOR SECOND LASER, LIKE A Ti:$\lambda_{1_2O_3}$, LASER

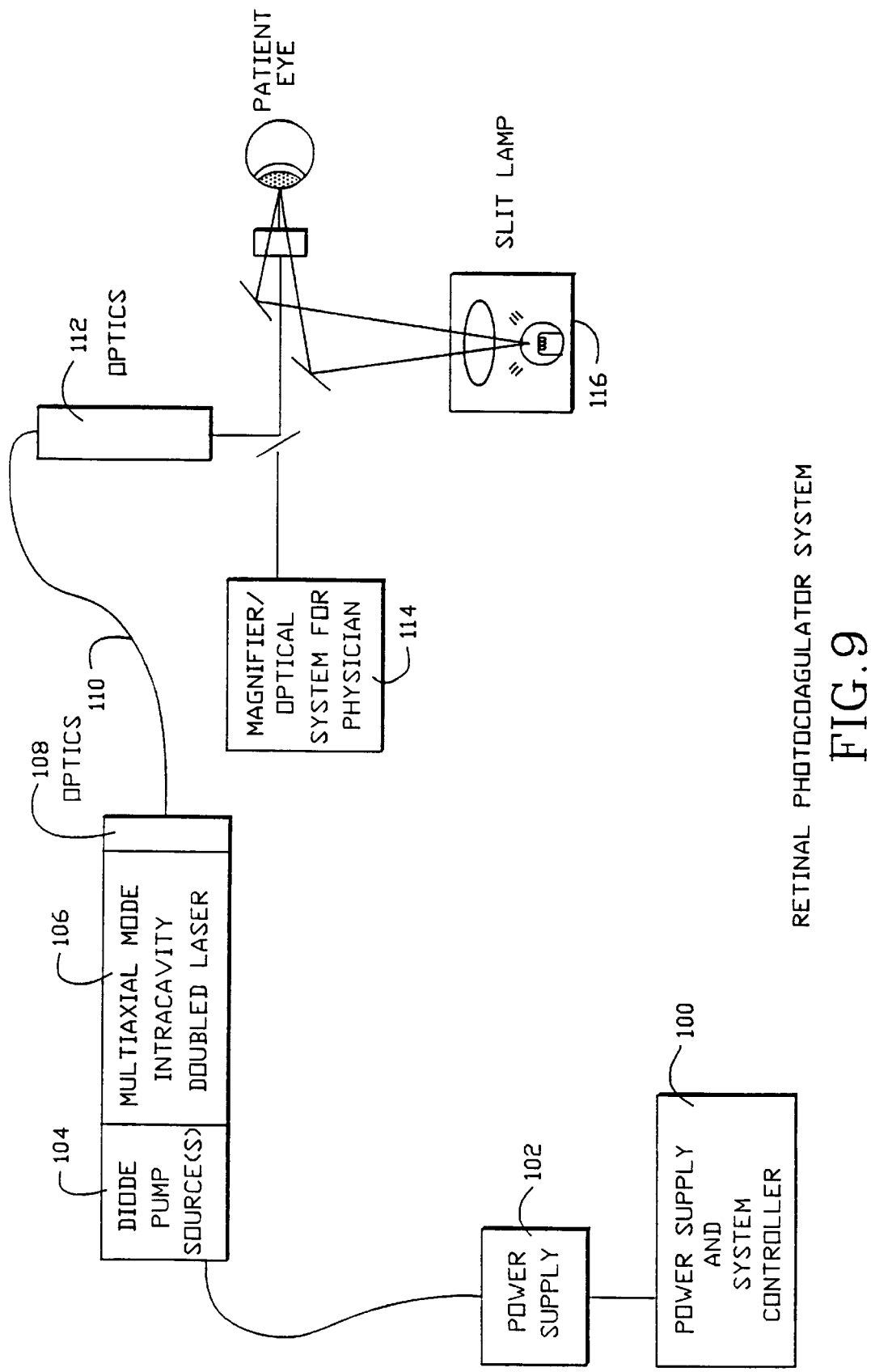

RETINAL PHOTOCOAGULATOR INCLUDING DIODE PUMPED, MULTI-AXIAL MODE INTRACAVITY DOUBLED LASER

CROSS-REFERENCE TO RELATED APPLICATIONS

This application is a continuation of U.S. patent application Ser. No. 08/446,203 entitled DIODE PUMPED, MULTI AXIAL MODE INTRACAVITY DOUBLED LASER, by Nighan et al., filed May 19, 1995, which is a continuation-in-part of U.S. patent application Ser. No. 08/191,656 now U.S. Pat. No. 5,446,749 entitled "DIODE PUMPED, MULTI AXIAL MODE, INTRACAVITY DOUBLED LASER" BY Nighan et al., filed Feb. 4, 1994, both of which are incorporated herein by reference.

This application also cross-references U.S. patent application Ser. No. 08/446,195 entitled "DIODE PUMPED, MULTI AXIAL MODE, INTRACAVITY DOUBLED LASER" by Nighan et al., filed May 19, 1995 (the same filing date as the present application).

BACKGROUND OF THE INVENTION

1. Field of the Invention

This invention relates generally to diode pumped intracavity frequency doubled lasers, and more particularly to continuous wave, diode pumped intracavity frequency doubled lasers that are multiaxial mode lasers which exhibit high amplitude stability.

2. Description of Related Art

Continuous wave ion lasers are relatively reliable sources of continuous wave green laser light with low amplitude noise, and provide output power at the multiple watt level. These devices convert electrical power into optical power with efficiencies of only a small fraction of one percent. There are many applications that would benefit from the development of a highly efficient, low cost, diode-pumped, continuous-wave, solid-state green, blue, red, near infrared, or UV laser source, also at the multiple watt level and with comparable amplitude stability.

Certain fundamental difficulties with intracavity-frequency-doubled solid-state lasers were discovered and numerically modeled in early work by Baer. See for example T. Baer, J. Opt. Soc. Am. B., Vol. 3, No. 9, pp. 1175–1180 (1986), and U.S. Pat. Nos. 4,656,635 and 4,701,929. It was reported and disclosed that large amplitude fluctuations are observed on the green output beam and the intracavity infrared laser beam when a frequency doubling crystal such as KTP is introduced into an otherwise amplitude-stable multiaxial mode diode-pumped Nd:YAG laser. It was also reported that the large amplitude noise on the green output beam disappears when an appropriate etalon is placed in the laser cavity that forces single axial mode oscillation. In the multiaxial mode case, where 2 to 4 modes were oscillating, the green output power was seen to fluctuate with up to 100% modulation depth. Baer's experimental work and theoretical model indicated that the insertion of a frequency doubling crystal in this multiaxial mode laser resulted in nonlinear coupling of the loss of the infrared axial modes via sum frequency generation. A high peak power in one axial mode induced a high nonlinear loss for the other axial modes, and caused an unexpected and undesirable pulsing effect.

As an example of the effect described by Baer, a laser with two infrared axial modes generated three green frequencies; two were doubled modes and the other a sum frequency mode. The sum frequency process couples the two infrared axial modes in a way that can cause them to switch on and off in a sequential fashion. The typical period of this mode coupling was found to be a function of the magnitude of the nonlinear conversion. For weak conversion, the period was short and the modes minimally modulated. For stronger conversion, the mode coupling period lengthened, and the modes switched on and off in pulses of high peak power, completely out of phase with each other in a semi-periodic fashion. The noise spectrum of such a laser typically showed substantial peaks in the 10 to hundreds of kHz range for either the green or infrared, and corresponded to considerable amplitude fluctuations.

A source with this type of amplitude modulation is not as generally useful as one with low amplitude noise, and therefore high amplitude stability. As an example, for applications in ophthalmology, such as retinal photocoagulation, amplitude stability is required on the time scale of the typical exposure durations for accurate control of therapeutic effects. Another example is the use of a green laser as a pump for a second laser, such as a dye or $Ti:Al_2O_3$ laser. Deep amplitude modulation at certain frequencies can cause undesirable amplitude modulations on the output of the second laser.

A number of methods for stabilizing the intracavity-frequency-doubled output of a diode-pumped solid-state laser have been described and demonstrated. The most common materials have been Nd:YAG as a laser medium and KTP as a nonlinear, doubling medium. For this reason, the most common type of phase matching is Type II. One technique that has been used in an attempt to stabilize the frequency doubled output from such systems included insertion of intracavity quarter wave plates (see M. Oka, and S. Kubota, Opt. Lett. 13, 805 (1988)). The Oka quarter-wave technique can result in two orthogonally polarized infrared eigenmodes that are not coupled by sum-frequency generation. The Oka configuration was shown to be amplitude-stable under certain conditions. However, for higher output powers this configuration requires the addition of an etalon (M. Oka et al, 1993 Advanced Solid State Laser Conference, paper AMG1). It was reported that this system could be stable for only a few hours at a time. The temperature control of the KTP is imperative with this technique. Other techniques used for stabilizing the output of intracavity-doubled solid-state lasers include optical cavity temperature control (see U.S. Pat. No. 4,884,277 issued to Anthon, et al. on Nov. 28, 1989) and forcing single frequency operation (see U.S. Pat. No. 5,164,947 issued to G. J. Lukas, et al. on Nov. 17, 1992, and W. Weichmnann et al., 1995 Advanced Solid State Laser Conference, papers TuD4 and WD4).

Another method of achieving low noise operation is also based upon single frequency operation: J. Nightingale et al have developed an intracavity-doubled unidirectional ring laser with diode-pumped Nd:YAG and KTP (U.S. Pat. No. 5,052,815, U.S. Pat. No. 5,136,597, and U.S. Pat. No. 5,170,409, and 1994 Compact Blue Green Laser Conference, Post-deadline paper PD6).

While all of these techniques have demonstrated regimes of operation where the frequency doubled output is measured to have low amplitude noise, in all cases the techniques are difficult to implement in a reliable, low cost fashion that is resilient to changes in environmental conditions, such as temperature. The techniques employed typically must maintain an inherently amplitude-unstable system within the narrow range of parameter space for which the system is stable. The single frequency intracavity-doubled systems can suffer mode-hops that result in undesirable discontinuities in output power. To avoid this, single frequency systems must be designed to be resistant to such mode hops. Additionally, the potential for scaling currently available systems to higher power may be limited.

It would be highly desirable to provide an inherently amplitude-stable, intracavity-frequency-doubled, solid-state laser that does not require active stabilization or single axial mode operation. Additionally, there is a need for a laser of this type that remains stable over a range of environmental conditions, such as changes in ambient temperature. There is a need for an intracavity-frequency-doubled laser that does not exhibit discontinuities in output power, as with single frequency systems. There is also a need for an amplitude stable, intracavity frequency doubled laser that can be scaled to higher powers. A similar frequency-tripled system would also be useful.

SUMMARY OF THE INVENTION

It is an object of the invention to provide a continuous-wave (CW), diode-pumped, multiaxial mode, intracavity-frequency-doubled solid-state laser with high amplitude stability.

Another object of the invention is to provide a CW, diode-pumped, multiaxial mode, intracavity-frequency-doubled laser with a percent root mean square noise (% RMS) of less than about 0.5% over a wide range of operating parameters.

A further object of the invention is to provide a CW, diode-pumped multiaxial mode, intracavity-frequency-doubled laser with a percent root mean square noise (% RMS) of less than about 0.5% over a wide range of operating parameters that utilizes the combination of $Nd:YVO_4$ and LBO, $Nd:YVO_4$ and another non-linear crystal, or LBO and another gain medium.

Still another object of the invention is to provide a CW, diode-pumped, intracavity-frequency-doubled laser with $Nd:YVO_4$, generating a doubled output power of 1 watt or greater.

Yet another object of the invention is to provide a diode-pumped, multiaxial mode, intracavity-frequency-doubled laser that utilizes diode bars.

Another object of the invention is to provide a diode-pumped, multiaxial mode, intracavity-frequency-doubled laser that utilizes fiber-coupled diode pump sources.

A further object of the invention is to provide a diode-pumped, multiaxial mode, intracavity-frequency-doubled laser that utilizes a laser crystal with strong thermal focussing properties.

Still a further object of the invention is to provide a diode-pumped, multiaxial mode, intracavity-frequency-doubled laser that utilizes a pump-beam spot in the laser crystal that is larger than the $TEM_{00}$ mode size in the laser crystal.

Yet another object of the invention is to provide a CW, diode-pumped, multiaxial mode, intracavity-frequency-doubled laser and intracavity-frequency-tripled laser with high amplitude stability that produces a blue or ultraviolet output.

A further object of the invention is to provide a CW, diode-pumped, multiaxial mode, intracavity-nonlinearly-converted laser, the nonlinear conversion mechanism including intracavity harmonic generation, optical parametric oscillation, optical parametric generation, and/or frequency mixing.

These and other objects of the invention are achieved in a CW, diode-pumped, multiaxial mode, intracavity-frequency-doubled laser with high amplitude stability. The laser includes at least two resonator mirrors defining a resonator cavity. A laser crystal and a doubling crystal are positioned in the resonator cavity. A diode pump source supplies a pump beam to the laser crystal, and produces a laser crystal beam with a plurality of axial modes. The axial modes are incident on the doubling crystal and produce a frequency doubled output beam with a %RMS noise of less than 1%.

The frequency doubled laser of the present invention can have an $Nd:YVO_4$ laser crystal, and an LBO doubling crystal. The output power of the laser can exceed 1 watt.

The frequency conversion laser of the present invention can include, (i) a doubling crystal positioned in the resonator cavity, (ii) a tripling crystal positioned in the resonator cavity, (iii) a nonlinear conversion apparatus positioned in the resonator cavity, (iv) a %RMS noise of less than 0.5%, (v) a %RMS noise of less than 0.2%, (vi) a %RMS noise of less than 0.1%, (vii) a pump source that is a diode bar or a plurality of diode bars, and/or (viii) a diode pump source that is fiber coupled.

Further, the frequency doubled laser of the present invention can be a pump source for a second laser, and it can also be used for ophthalmic applications. The multi-axial mode apparatus can be used in other forms of intracavity nonlinear conversion, including but not limited to intracavity harmonic generation, optical parametric generation and/or frequency mixing.

With the present invention, a large number of axial modes oscillate, with as few as on the order of 10 and as many as about 200, preferably about 100. With this configuration, the relative power in each axial mode is smaller than in the case of 2 to 4 axial modes. The relative magnitude of the nonlinear coupling of the axial modes is therefore reduced. However, the statistical probability of coupling of one mode to some other mode via sum frequency generation is increased, since the number of modes is increased. With the present invention, none of the characteristic spiking behavior, as observed by Baer in his early work, is observed for any of the individual axial modes of the large number that are oscillating. This indicates that with the present invention no one axial mode is able to reach a high peak power and induce a high nonlinear loss for the other axial modes. Thus, the present invention provides the oscillation of a large number of axial modes and results in a highly amplitude stable output beam.

While each individual axial mode may not exhibit high amplitude stability, the composite output beam, which is the superposition of many doubled and summed axial modes, exhibits very high amplitude stability. As previously stated, the RMS nose can be lower than 0.5%, and even as low as 0.1%. In some cases, the RMS noise of the present invention can be lower than that measured for a standard argon ion laser at the same output power level.

In one embodiment, a fiber-bundle-coupled diode bar is used to longitudinally pump Nd:YLF crystals with up to 9 W per crystal. The fast axis divergence of the diode bar is reduced by a cylindrical microlens, U.S. Pat. No. 4,785,459, issued to Baer, and each emitting array of the bar is coupled into a multimode optical fiber. This highly bright pump source is described in U.S. Pat. No. 5,127,068, issued to Baer et al. on Jun. 30, 1992. Output power is extracted from the laser resonator by intracavity frequency doubling. The nonlinear crystal can be lithium triborate, or LBO, and Type I noncritical phase matching (NCPM) can be used. The output power is typically on the order of 2 W or greater for 16 W of incident diode pump light from a single 20 W, CW, ~797 nm diode laser bar. This corresponds to an optical efficiency ($P_{out}/P_{incident}$) of approximately 12.5%. Including a fiber bundle transfer efficiency of 85%, and a diode electrical power to optical efficiency of 40%, the electrical diode power to optical efficiency of the intracavity frequency doubled laser utilizing Nd:YLF is on the order of 4.25%. This is a large number in comparison to small fraction one percent that is typical for green ion laser sources.

In another embodiment, power scaling is accomplished with the use of two such fiber-bundle-coupled diode bars used to pump an Nd:YVO$_4$ laser crystal or crystals. Further, an intracavity-doubled Nd:YVO$_4$ laser with doubled output greater than 1 W and nearly diffraction-limited output is produced. In the high power Nd:YVO$_4$ embodiments, optimum performance is typically achieved when the pump beam size in the laser crystal is slightly larger than the size of the TEM$_{00}$ mode in the laser crystal. This is in opposition to the teachings of classic mode-matching of diode-pumped solid-state lasers, in which the pump beam size is typically somewhat smaller than that of the TEM$_{00}$ mode. The mode size can be as small as 0.8 of the pump beam size. This ratio is optimal because of strong aberrations in the thermal lens in the Nd:YVO$_4$.

In a high power Nd:YVO$_4$ embodiment, approximately 26 W of total pump power is used to excite the laser crystal, with ~13 W incident upon each end of the crystal. Multiple laser crystals can also be used. An LBO crystal is used for frequency doubling the intracavity infrared beam that is emitted by the laser crystal or crystals. The output power is typically on the order of 6 W of green in a TEM$_{00}$ mode, which corresponds to an optical efficiency ($P_{out}/P_{incident}$) of approximately 23%. Including a fiber bundle transfer efficiency of 85%, and a diode-electrical-power-to-optical-power-efficiency of 40%, the electrical-diode-power-to-optical-output-power-efficiency of the intracavity frequency doubled laser is on the order of up to 16%. If TEM$_{00}$ is not required, or if very low noise is not required, up to 8 W of 532 nm output can be obtained for the same 26 W of pump power, representing even higher efficiency. An aperture is typically required for TEM$_{00}$ operation. When optimized for low noise, i.e., high amplitude stability, the RMS noise can be lower than 0.5% for a 6 W frequency-doubled output. Typically, the output beam is substantially TEM$_{00}$ in this case. If care is taken to eliminate acoustic noise associated with vibration or water cooling, RMS noise on the order of 0.2%, or less, is achieved. The highly amplitude stable output of these lasers is relatively insensitive to environmental parameters, such as temperature.

In these embodiments of this invention, the green or doubled output beam is substantially round since Type I, non critical phase matching (NCPM) is employed, which provides a large acceptance angle and minimizes walk-off, as will be recognized by those of ordinary skill in the art. This is very helpful when a "double pass geometry" is employed. If a nonlinear crystal with nonzero walkoff is used, like KTP, the double pass geometry can result in an imperfect overlap between the two doubled beams; one beam is generated upon the first pass, the second on the second pass. The nonlinear crystal lithium triborate, LBO, is used. The phase matching and doubling efficiency are optimized by optimizing the crystal temperature in the vicinity of 145 to 175° C., with ~155° C. being typical for conversion of 1064 nm to a 532 nm harmonic. In certain embodiments, the green beam and infrared beam are nearly diffraction limited, and the RF noise spectrum shows no heterodyne peaks other than the primary c/2L peak at about 140 MHz. This indicates that the laser oscillates on its lowest order spatial mode. The RMS noise from 10 Hz to 10 MHz can be lower than 0.5%, and even 0.1% or less, although even a noise lower than 3% RMS can be useful. An aperture is typically used to insure TEM$_{00}$ operation with high amplitude stability in the Nd:YVO$_4$ embodiment.

The nonlinear crystal KTP can be used for intracavity doubling in conjunction with the multiaxial mode techniques of the present invention. Care is taken to insure phase-matching and appropriate polarization rotation as identified by Nightingale et al. and Wiechmann et al. The combination of these techniques with the multiaxial mode doubling of the present invention achieves a robust, low noise, doubled output beam. In one embodiment, using Nd:YVO$_4$ pumped by 26 W of diode pump power from two fiber-coupled diode bars and a resonator configuration similar to that used with LBO, approximately 5 W of TEM$_{00}$ output at 532 nm is generated with approximately 0.5% RMS noise. The orientation, angle, and temperature of the KTP crystal must be optimized for a Type II intracavity interaction that preserves the polarization of the eigenmode upon one round trip of the cavity.

BRIEF DESCRIPTION OF THE FIGURES

FIG. 9 is a schematic diagram of a retinal photocoagulator system incorporating a diode pumped, multi axial mode, intracavity frequency doubled laser used as a laser source.

DETAILED DESCRIPTION

Figure 1:
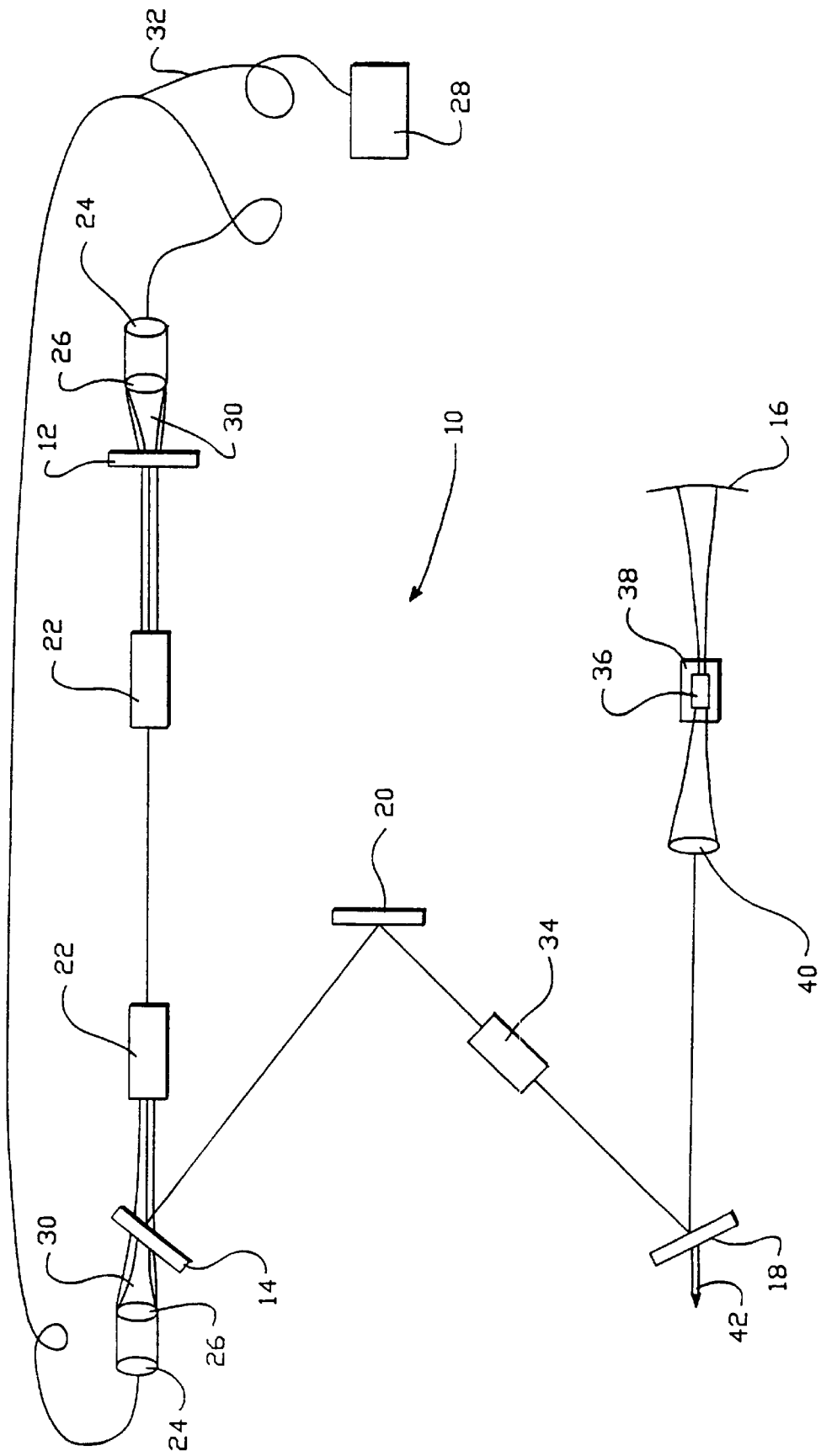
FIG. 1 is a schematic diagram of a multi-port, diode pumped, multiaxial mode, intracavity doubled laser resonator with high amplitude stability.
Figure 2:
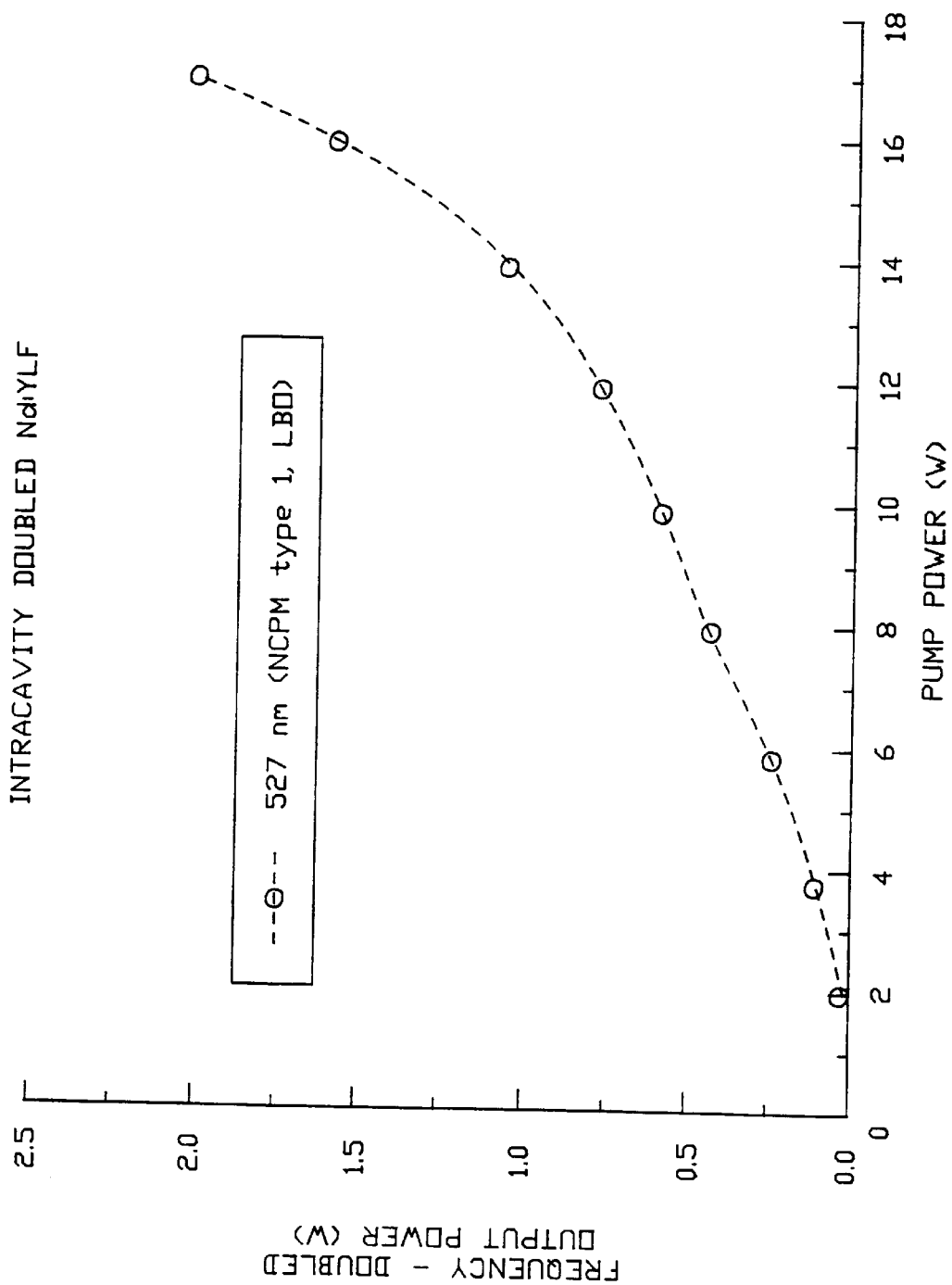
FIG. 2 is a graph illustrating frequency doubled output power as a function of incident optical input power of the laser resonator shown in FIG. 1.

For the purposes of the following description of the invention, the following definitions are used:

a "high power" frequency doubled output as an output power ($P_{out}$) equal to or greater than 1 watt.

a "high optical efficiency" as an optical-to-optical efficiency ($P_{out}/P_{incident,\ diode}$) that is greater than 5%. The optical pump power from the laser diode that is incident on the laser crystal is ($P_{incident,\ diode}$). In the case of the fiber-coupled diode pump sources, the value of ($P_{incident,\ diode}$) is the power that is emitted by the fibers.

a "high electrical to optical efficiency" for a diode pumped intracavity frequency doubled laser as an efficiency ($P_{out}/P_{electrical.diode}$) greater than 1%. The value of ($P_{electrical,\ diode}$) is the value of electrical power provided to the diode, in the form of the operating current times the voltage drop across the laser diode. The value of ($P_{electrical,\ diode}$) for a 20 W diode bar is typically 2.5 times that of the optical output power of the diode bar; these bars are typically 40% efficient. For this estimation of high electrical efficiency, the amount of power required to cool the diodes is not included; in some cases it may be necessary to consider this power.

a "multiaxial" mode intracavity frequency-doubled laser as a laser where on the order of 3 or more axial modes are oscillating at the fundamental infrared wavelength in the laser resonator. In some cases, the number is on the order of 100 to 200.

a "highly amplitude stable" intracavity frequency doubled laser, or the same laser with "high amplitude stability" as one where the output beam exhibits percent root mean square (% RMS) noise from 10 Hz to 10 MHz of less than 3%. In a preferred embodiment, this noise level can be as low as 0.2%, high amplitude stability is equated with low amplitude noise.

The diode-pumped, multiaxial mode, intracavity-doubled laser of the present invention includes at least one laser crystal and at least one doubling crystal positioned in a resonator cavity. This laser is highly amplitude stable, and the frequency-doubled output beam is of high power. A diode pump source supplies a pump beam to the laser crystal and produces an intra-cavity, infrared laser crystal beam at a plurality of axial modes that is incident upon the doubling crystal, producing a frequency-doubled output beam, also at a plurality of optical frequencies. The output beam is highly amplitude stable, meaning that the %RMS noise is less than 1%, preferably less that 0.5%, more preferably less than 0.2% and most preferably less than 0.1%. The laser is highly optically efficient, with an optical efficiency greater than 5% and preferably greater than 12%, with a preferred Nd:YVO$_4$ embodiment at about 23%. The laser is highly electrically-to-optically efficient, with an electrical-to optical efficiency greater than 1%, and preferably greater than 4%, with a preferred Nd:YVO$_4$ embodiment at about 8%. The systems are typically configured to provide good beam quality, meaning that a substantial fraction of the output power is nearly diffraction limited, or is substantially TEM$_{00}$.

In FIG. 1, a bounded, standing wave resonator 10 for 1053 nm is illustrated. Resonator 10 is multi-port and diode pumped with four arms, each arm with its own optical axis. The first arm is defined by a high reflector 12, which is highly reflecting at 1053 nm and highly transmissive at a pump wavelength of 797 nm, and a high reflector 14, which is highly reflecting at 1053 nm and highly transmissive at 797. The distance between reflectors 12 and 14 is L1. The second arm of resonator 10 is defined by a high reflector 16, highly reflecting at 1053 nm, and highly reflecting at 527 nm, and an output coupler 18, highly reflecting at 1053 nm and highly transmissive at 527 nm. It has a length of L2. The third arm, with a length of L3, is defined by high reflector 14 and a high reflector 20, which is highly reflecting at 1053 nm. High reflector 20 is, essentially, a fold mirror. The fourth arm, with a length of L4, is defined by high reflector 20 and output coupler 18. An optional Brewster plate 34 can be placed in this arm. Although the optical elements in this embodiment are specific for 1053 nm, 797 nm and 527 nm, it will be appreciated that the optical elements can have other transmission and reflectivity characteristics, depending on pump source, laser crystal and doubling crystal.

The length of resonator 10 is L, and it equals the total lengths of the four arms. The optical path length of the resonator is very close to L. It differs from the sum of the lengths of the four arms only because of any optically dense material in the cavity, as is well known. For example, a laser crystal of length $L_c$ and index $n_c$ at a given wavelength has an optical path length of $n_c L_c$ at that wavelength, as is well known to those skilled in the art.

One or more laser crystals 22 are positioned in the first arm along its optical axis. Suitable crystals include but are not limited to Nd:YLF, Nd:YAG, Nd:YVO$_4$, Nd:GVO$_4$, Nd:YPO$_4$, Nd:BEL, Nd:YALO, and Nd:LSB and Nd:YVO$_4$. A preferred crystal material is Nd:YVO$_4$ particularly as illustrated in FIGS. 3 through 7. Positioned adjacent to reflectors 12 and 14 are a pair of lenses 24 and 26, arranged in a telescope configuration. The output of a fiber-coupled diode pump source 28 produces a pump beam 30 that is focussed to a desired size by lenses 24 and 26. The telescope arrangement provides for the focussing of pump beam 30 from a diode source 28. The size of the pump beam is optimized with lenses 24 and 26 to avoid fracture of incident faces of crystals 22 while increasing useful pump power. The TEM$_{00}$ mode size diameter of the infrared beam in the laser crystals is about 1 millimeter in an embodiment that utilizes Nd:YLF, but is about 0.5 mm in an embodiment that utilizes Nd:YVO$_4$. The pump beam diameter is about 0.6 to 0.7 mm in either embodiment. This pumping geometry is longitudinal pumping, or end pumping, as will be recognized by those skilled in the art. It is clear that an amplitude stable, multi-axial mode, intracavity doubled laser also extends to transversely pumped systems, or directly-pumped systems that do not use fiber-coupled diodes.

Diode pump source 28 can be a single diode, spatial emitter, diode bar or a plurality of diodes or A plurality of diode bars that have a reduced fast-axis divergence.. A suitable diode source 28 is model No. OPC-A020-797-CS, available from OptoPower Corporation, City of Industry, Calif. Another suitable diode is denoted as BO2O. Preferred wavelengths of diode pump source 28 are in the range of 795 to 815 nm. Peak absorption wavelengths of specific laser crystals 22 are approximately as follows: Tm:YAG—785 nm; Nd:YLF—797; and Nd:YAG, Nd:YVO$_4$—809 nm. The "797" designator in the OptoPower product number becomes "809" when an 809 nm wavelength is desired. As is now well known in the art, the wavelength of the output of such an GaAlAs based diode can be tuned by adjusting the temperature of the diode. The tuning rate is well-known to be about 0.3 nm/° C.

In the embodiment of FIG. 1, two laser crystals 22 are longitudinally-pumped, or end pumped. It is possible to include only one crystal and pump both ends, as in FIGS. 5 through 7, or alternatively, pump only one side of a single crystal 22, as in FIGS. 3 and 4. As shown in FIG. 1, a single diode pump source 28 is used. Separate pump sources can be used for each end of the first arm of resonator 10, or for the resonators in FIGS. 5 through 7. It will be appreciated that the principles of stable, multiaxial mode intracavity doubling also extend to transversely-pumped, or side-pumped lasers.

Diode pump source 28 is coupled to one or more optical fibers 32. Preferably, a bundle of optical fibers 32 are utilized. Suitable fibers include but are not limited to those that have silica cores with silica cladding.

In one embodiment, a fiber-bundle-coupled diode bar is used to longitudinally pump Nd:YLF crystals with up to 9 W per crystal. The fast axis divergence of the diode bar is reduced by a cylindrical microlens, U.S. Pat. No. 4,785,459, issued to Baer, and each emitting array of the bar is coupled into a multimode optical fiber. This highly bright pump source is described in U.S. Pat. No. 5,127,068, issued to Baer et al. on Jun. 30, 1992. Output power is extracted from the laser resonator by intracavity frequency doubling. The nonlinear crystal can be lithium triborate, or LBO, and Type I noncritical phase matching (NCPM) can be used. The output power is typically on the order of 2 W or greater for 16 W of incident diode pump light from a single 20 W, CW, ~797 nm diode laser bar. This corresponds to an optical efficiency ($P_{out}/P_{incident}$) of approximately 12.5%. Including a fiber bundle transfer efficiency of 85%, and a diode electrical power to optical efficiency of 40%, the electrical diode power to optical efficiency of the intracavity frequency doubled laser is on the order of 4.25%. This is a large number in comparison to a small fraction of one percent that is typical for ion laser sources.

Optionally included in resonator 10 is a Brewster plate 34 or other polarizing device, which can be used to insure operation at a particular polarization. This is particularly useful when Nd:YAG is used for the gain medium. Brewster plate 34 can be positioned along the optical axis of either the third or fourth arms. A doubling crystal 36 is positioned in the second arm. In one embodiment, doubling crystal 36 is LBO. Other suitable doubling crystals include KTP, KDP, BBO, LBO, $LiNbO_3$, and $KNbO_3$. When LBO is used, a heating element 38 is included. A suitable heating element 38 is a resistive heater or a thermoelectric device as available from Melcor, Trenton, N.J. 08648.

LBO doubling crystal 36 is used in a Type I, non-critical-phase-matched (NCPM) geometry, where the phase-matching is controlled with temperature, typically about 145 to 175° C. when doubling from 1.053–1.064 μm to 527–532 nm. A typical temperature is 155° C. The high acceptance angle of non-critical-phase-matching (NCPM) in LBO doubling crystal 36 allows resonator 10 to be adjusted in a manner that yields high beam quality and nearly $TEM_{00}$ operation. Other types of phase matching may not preserve beam quality with tight focussing, which can cause multi-spatial mode behavior, or elliptical doubled beams.

In these embodiments of this invention, the green or doubled output beam is substantially round since Type I, non critical phase matching (NCPM) is employed, which provides a large acceptance angle and minimizes walk-off, as will be recognized by those of ordinary skill in the art. This is very helpful when a "double pass geometry" is employed. If a nonlinear crystal with nonzero walkoff is used, like KTP, the double pass geometry can result in an imperfect overlap between the two doubled beams; one is generated upon the first pass, the second through the second pass. The nonlinear crystal lithium triborate, LBO, is used. The phase matching and doubling efficiency are optimized by optimizing the crystal temperature in the vicinity of 145 to 175° C., with ~155° C. being typical for conversion of 1064 nm to a 532 nm harmonic.

When Nd:YLF is used as laser crystal 22, and the size of pump beam 30 in the crystal 22 is optimized, a substantially $TEM_{00}$ output beam can be generated even without an intracavity aperture. However, when other gain media are used, an aperture must sometimes be used if $TEM_{00}$ operation is desired.

In another embodiment, power scaling is accomplished with the use of two such fiber-bundle coupled diode bars used to pump an $Nd:YVO_4$ laser crystal. Further, an intracavity-doubled $Nd:YVO_4$ laser with output greater than 1 W and nearly diffraction-limited output is produced. In the high power $Nd:YVO_4$ embodiments, optimum performance is typically achieved when the pump beam size in the laser crystal is slightly larger than the size of the $TEM_{00}$ mode in the laser crystal. This is in opposition to the teachings of classic mode-matching of diode-pumped solid-state lasers, in which the pump beam size is typically somewhat smaller than that of the $TEM_{00}$ mode. The mode size can be as small as 0.8 of the pump beam size. This configuration is optimal because of strong thermal aberrations in the end-pumped laser crystal. This is also true for other materials with strong thermal focussing characteristics, including but not limited to Nd:YAG.

The output power is typically on the order of 6 W of green in a $TEM_{00}$ mode, which corresponds to an optical efficiency ($P_{out}/P_{incident}$) of approximately 23%. Including a fiber bundle transfer efficiency of 85%, and a diode electrical power to optical efficiency of 40%, the electrical diode power to optical efficiency of the intracavity frequency doubled laser is on the order of 8%. If $TEM_{00}$ is not required, or if very low noise is not required, up to 8 W of 532 nm output can be obtained for the same 26 W of pump power, representing even higher efficiency. When optimized for low noise, i.e., high amplitude stability, the RMS noise can be lower than 0.5% for a 6 W frequency-doubled output. Typically in the embodiment, the output beam is substantially $TEM_{00}$. If care is taken to eliminate acoustic noise associated with vibration or water cooling, RMS noise on the order of 0.2%, or less, can be achieved. The highly amplitude stable output of these lasers is relatively insensitive to environmental parameters, such as temperature.

In certain embodiments, the green beam and infrared beam are nearly diffraction limited, and the RF noise spectrum shows no heterodyne peaks other than the primary c/2L peak at about 140 MHz. This indicates that the laser oscillates on its lowest order spatial mode. The RMS noise from 10 Hz to 10 MHz can be lower than 0.5%, and even 0.1% or less, although even a noise lower than 3% RMS can be useful. An aperture is typically used to insure $TEM_{00}$ operation with high amplitude stability in the $Nd:YVO_4$ embodiment High amplitude stability is maintained for tilting of the LBO crystal to either side of normal, for translation of the Z position of the LBO doubling crystal 36 and/or high reflector 16, and temperature tuning the LBO by +/−3 C of the optimum temperature. These adjustments sacrifice a small amount of useful output power of resonator 10. In a preferred embodiment, the ends of the LBO crystal 36 are cut and polished to be non-parallel to one another and non-normal to the infrared intracavity beam propagation direction through the LBO crystal 36. Any spurious reflection from the surfaces of LBO crystal 36 that strikes the end mirror 16 can degrade the amplitude stability of the doubled output beam. These spurious beams can strike the end mirror and then couple back into the main beam of the cavity, creating a undesirable degradation in performance. It is important to prevent these spurious beams from coupling back into the main intracavity beam. It is possible to use an aperture between crystal 36 and end mirror 16 to operate in this function.

Pump beam 30 passes through laser crystals 22 and an intra-cavity infrared laser crystal beam is created. The laser crystal beam is then incident upon a face of LBO crystal 36. In the laser of FIG. 1, a small waist, on the order of about 50 μm diameter, is preferably generated inside LBO doubling crystal 36 in order to produce a very high intensity infrared beam within LBO crystal 36. High intensity is needed because the conversion of infrared to green increases nonlinearly (as the square) with the infrared intensity. LBO crystal 36 is antireflection coated at both the infrared and doubled wavelength, as is typical for an intracavity doubled laser. These coated crystals are available from Fujian-Castech in China The coating on LBO crystal 36 must provide very low reflectance at ~1.064 µm, such as <1%, and preferably <0.1%. The coating should also provide relatively low reflectance at 532 nm, such as <1% or better. Further, the coating must handle the high average power densities within the laser. The infrared laser crystal beam is focussed to the much smaller waist diameter by the inclusion of a lens 40 between output coupler 18 and LBO doubling crystal 36 and by the use of a high reflector 16 that has focussing powers. A suitable lens 40 is antireflection coated at the infrared and doubled wavelength, and is of focal length 30 to 50 mm.. High reflector 16 has a radius of curvature, R1 of about 100 mm.

The infrared laser crystal beam (for Nd:YLF its wavelength is 1.053, for NdYVO$_4$ it is 1064 nm), travels in two directions in the fourth arm of resonator 10. It travels from output coupler 18 through lens 40 and LBO doubling crystal 36 to high reflector 16, and is reflected from high reflector 16 back through the doubling crystal. As a result of this double-pass through LBO crystal 36, an output beam at 527–532 nm is generated. Because output coupler 18 is highly transmissive at 527–532 nm, an output beam 42 at 527–532 nm is generated by resonator 10. 527–532 nm light is generated in the fourth arm in two directions, relative to LBO doubling crystal 36, 527–532 nm light in the right hand direction, and 527–532 nm light in the left hand direction. The positioning of LBO doubling crystal 36 in the fourth arm between output coupler 18 and high reflector 16 creates a double pass geometry because 527–532 nm light is generated in both directions, and output beam 42 is the sum of these beams. The relative phases of the 1.053–1.064 µm beam and the 527–532 nm beam are important; the two beams are phase-shifted with respect to one another by double-passage through the air in between crystal 36 and mirror 16. The mirror coating on mirror 16 adds a further phase shift. This effect is known in the art; see for example Koechner, *Solid State Laser Engineering*, Vol. 3, p. 534. The net phase shift is ideally a multiple of 2π after this roundtrip, in order that the 1.053 µm (1064) beam and the 527–532 nm beam are in phase for the second trip through the doubler crystal 36. Some compensation for an imperfect multiple of 2π can be accomplished by adjusting the temperature of the doubling crystal 36. This effectively optimizes the overall phase-matching between the 1.053 nm beam and the 527 nm beam. This technique clearly extends to other wavelength pairs as well (i.e. 1.064 µm to 532 nm, 1.34 µm to 670 nm, 1.047 µm to 523 nm, etc.)

In one embodiment using resonator 10 of FIG. 1, fiber-bundle-coupled diode bars are used for diode source 28 to longitudinally pump Nd:YLF laser crystals 22 with up to 8 W per Nd:YLF crystal. Useful output power is extracted via intracavity frequency doubling and can result in more than 2 W output power at 527 nm for 16 W of incident pump light from a single 20 W CW diode laser bar. Output beam 42 is substantially round and is of high quality. Doubling efficiency can be fine tuned by varying the temperature of LBO doubling crystal 36 from a preferred temperature of about 140 to 175° C. Both the 527 nm output beam 42 and the infrared laser crystal beam are nearly diffraction-limited. The RF spectrum indicates that under certain conditions substantially no heterodyne peaks other than the c/2L peak at nearly 140 MHz are present, indicating that resonator 10 is oscillating on its lowest order spatial mode. This can typically be accomplished without an aperture when Nd:YLF is used as laser crystal 22, but a standard aperture is sometimes needed to insure TEM$_{00}$ operation, as is usually the case when Nd:YVO$_4$ is used.

In this embodiment, resonator 10 has a length L of about 1 m. L is the optical path length of the entire resonator. L is nominally equal to the total of L1, L2, L3 and L4. Additionally, resonator 10 exhibits the lowest amplitude noise when resonator alignment, LBO doubling crystal 36 angle, and LBO doubling crystal 36 temperature are adjusted in a way that results in primarily a single peak at the c/2L frequency in the RF spectrum. LBO doubling crystal 36 can be slightly off of normal incidence with respect to the cavity mode for this effect. In this state, the % RMS noise is as low as less than 3%, preferably less than 2%, and most preferably less than about 1%, as measured by a standard RMS meter over a range of 10 Hz to 10 MHz.

Additionally, in this embodiment, the optical spectrum of resonator at both the 527 nm output beam and the 1053 nm laser crystal beam indicates that typically at least 10 axial modes are oscillating at any one time, and as many as ~100 or more axial modes may be oscillating. The bandwidth of the intracavity infrared laser beam is about 35 GHz while 527 nm is produced, indicating that 100–200 axial modes can oscillate, and for certain alignment configurations the optical spectrum can have a structure indicating that the LBO doubling crystal 36 may be acting like an etalon. With the LBO doubling crystal 36 removed, the infrared axial mode spectrum stabilizes, with about 10 axial modes oscillating, and a bandwidth of about 30 GHz. The c/2L mode spacing is about 150 MHz for a 1 meter long resonator cavity 10. The 527 nm output beam 42 has a bandwidth of about >70 GHz.

As more infrared power from laser crystals 22 is generated, more frequency doubled output power can be obtained. Additional pumping ports and pump sources or other laser crystals, such as Nd:YVO$_4$ can facilitate scaling. Nd:YAG can also be used, typically in conjunction with an intracavity polarizing device. To achieve high amplitude stability, we find that a large number of infrared axial modes must oscillate. With Nd:YLF as the active medium, this was achieved with the ~1 meter long cavity. The cavity length (or resonator length) of diode pumped resonators for intracavity doubling of the prior art were typically very short, at typically less than 10 cm. Short lengths increase the c/2L axial mode spacing, and therefore typically decrease the number of axial modes that can oscillate within the available bandwidth of the laser crystals. Another technique for broadening bandwidth would utilize a broad bandwidth material, like Nd:LMA. Another resonator structure that would provide a long resonator length and many axial modes would be a resonator structure that includes an optical fiber. A very small c/2L spacing could be accomplished with a long fiber, placed intracavity with appropriate coupling optics.

Figure 3:
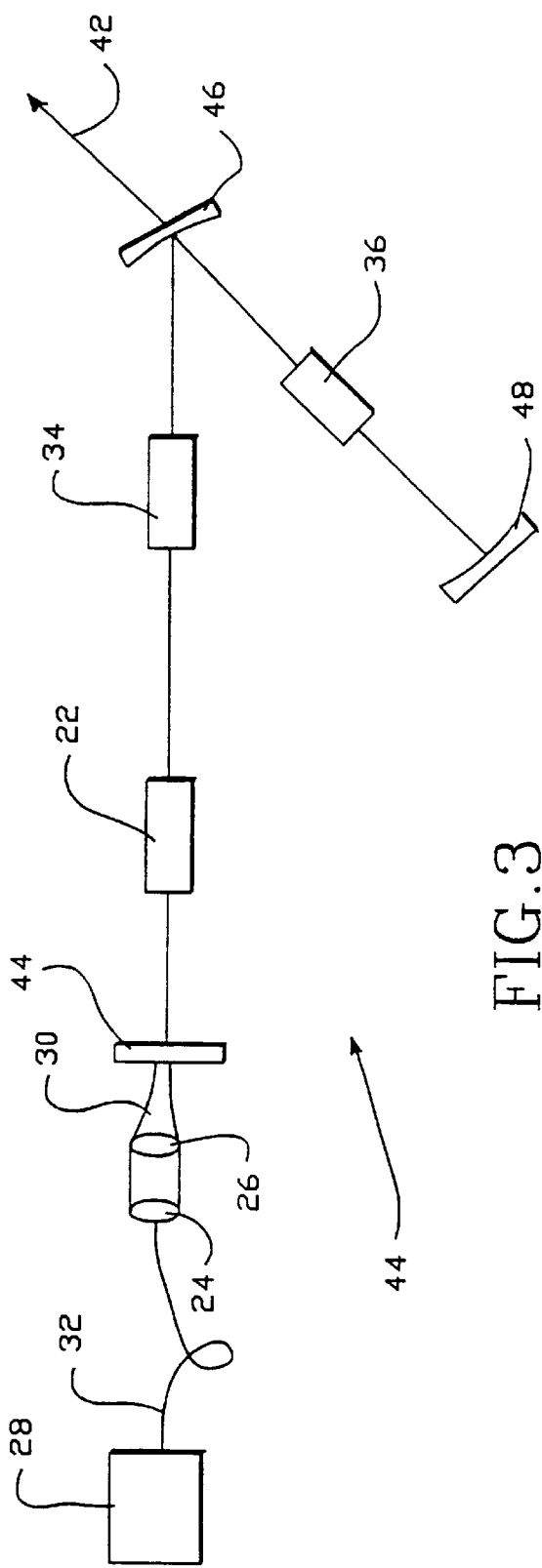
FIG. 3 is a schematic diagram of a single port, diode pumped, multiaxial mode, intracavity frequency doubled laser with high amplitude stability.

Resonator 44, illustrated in FIG. 3, has a simpler geometry than resonator 10 of FIG. 1. Resonator 44 includes a first arm that is defined by a high reflector 44 and an output coupler 46. Positioned along an optical axis of the first arm is laser crystal 22. A diode pump source 28 delivers pump beam 30 through optical fiber 32, or a bundle of fibers. Lenses 24 and 26 focus pump beam 30 so it is incident on laser crystal 22, and a laser crystal beam is produced. The second arm of resonator 44 is defined by output coupler 46 and a high reflector 48. Resonator 44 has a length L that is equal to the total lengths of the first and second arms. Positioned along an optical axis of the second arm is a doubling crystal 36. An optional Brewster plate 34, or polarizing device, can be positioned in resonator 44 such as in the first arm. The inclusion of Brewster plate 34 or another polarizing device is particularly desirable when Nd:YAG is used.

The laser crystal beam is reflected from output coupler 46 and is incident on doubling crystal 36. The second arm provides a double pass geometry for the generation of the frequency doubled output beam 42. If LBO is used as doubling crystal 36, then a heating element, not shown, is necessary. Additionally not illustrated in FIG. 3 is a lens disposed between doubling crystal 36 and output coupler 46. Inclusion of the lens is dependent on the type of doubling crystal 36 used, and on the radius of curvature and focussing power of high reflector 48 and output coupler 46.

Figure 4:
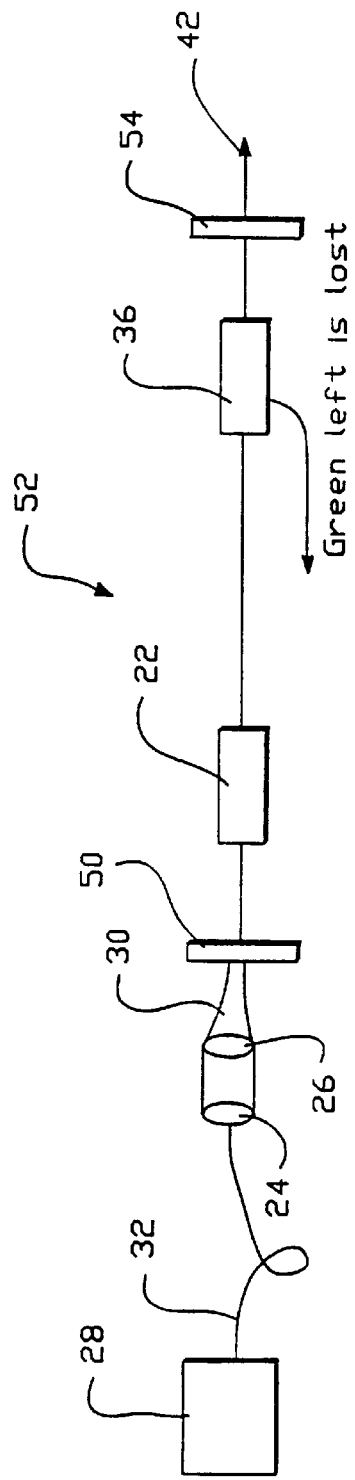
FIG. 4 is a schematic diagram of a single port, diode pumped, multiaxial mode, intracavity frequency doubled laser with high amplitude stability where a portion of the generated frequency doubled light is lost.

Resonator 52, shown in FIG. 4, does not include fold arms. Resonator 52 does not provide for a double pass geometry of the infrared beam through doubling crystal 36, and a portion of frequency doubled output beam 42 is lost in resonator 52. Again, through doubling crystal 36 frequency doubled output beam 42 is generated in both directions. However, with resonator 52, the portion of frequency doubled output beam 42 traveling to the left of doubling crystal 36 is lost.

Figure 5:
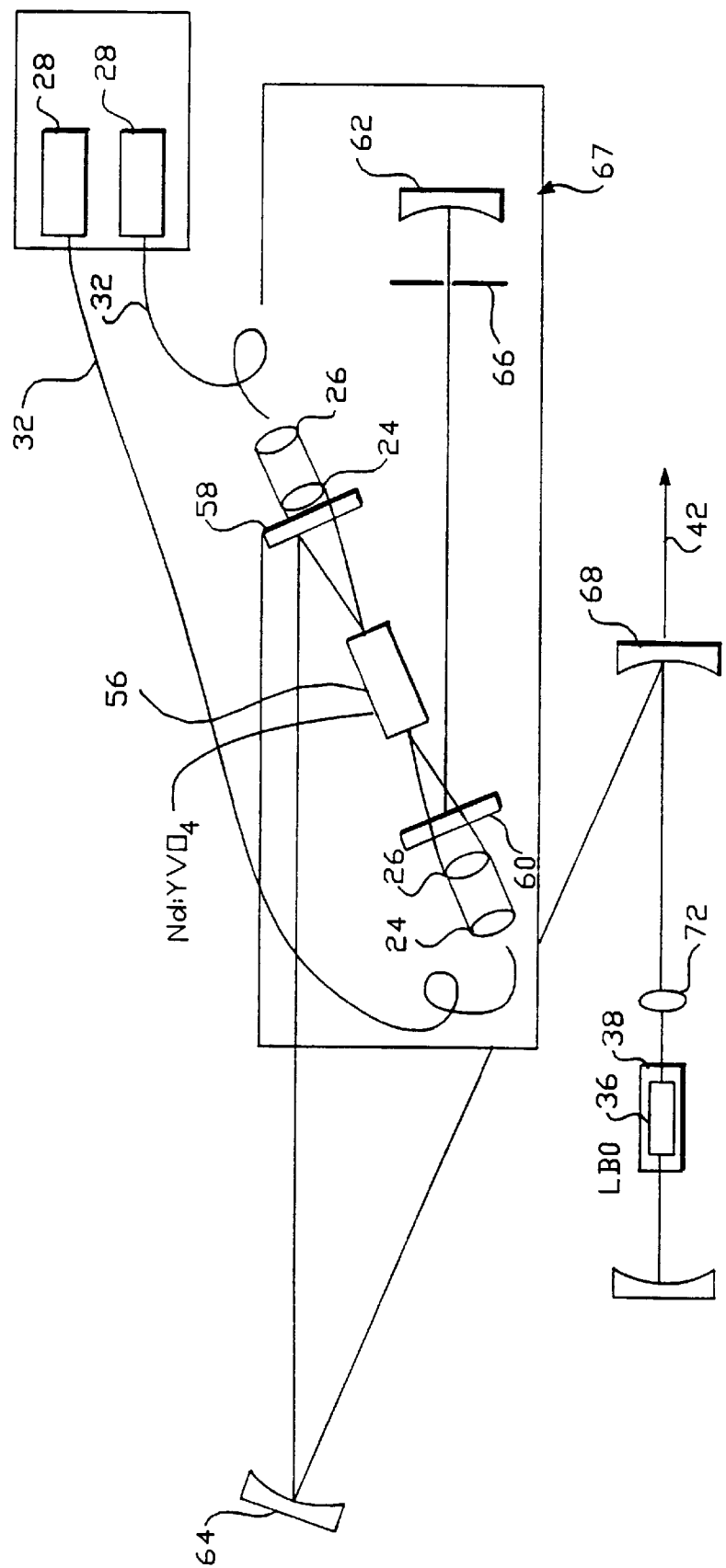
FIG. 5 is a schematic diagram of a two port, diode pumped, multiaxial mode, intracavity frequency doubled laser that utilizes Nd:YVO$_4$ and LBO.

As shown in FIG. 5, a power supply is included and is associated with diode modules 28. Each diode module 28 can be a 20 watt diode bar, commercially available from OptoPower. Diode modules 28 are coupled to a fiber bundle 32. Each fiber bundle 32 is connected to the resonator with a quick disconnect. The quick disconnect is in the vicinity of lenses 24 and 26, which image the output of each fiber bundle 32 into the Nd:YVO$_4$ crystal 56. This imaging is achieved through pump windows 58 and 60 which are coated with standard optical coatings and are highly transmissive at the pumping wavelength of approximately 809 nm, but highly reflective at the intra cavity wavelength of 1.064 microns. A standard multilayer dielectric coating is used, and is commercially from the Components and Accessories Group of Spectra-Physics Lasers, Mountain View, Calif. Pump sources 28 pump nominally along the longitudinal axis of a Nd:YVO$_4$ crystal. The region around the Nd:YVO$_4$ crystal of this resonator is in a "Z" configuration, and a mirror 28 is positioned at the end of the infrared section of the resonator. An apparatus 68 is utilized to ensure operation in the resonators lowest order spatial mode. Mirror 62 is highly reflective at 106 and may include a curvature of about 60 cm.

Mirrors 58 and 60 are flat, and the Z configuration defined by 58, 60 and 62 can be in the form of an infrared module 67, or an infrared laser, in which the output coupler has been removed. Infrared module 67 is then inserted into a larger laser. It will be appreciated, however, that a separate infrared module 67 need not be included. Instead mirrors 58,60 and 62 may be incorporated into the larger laser. Following the beam path it strikes mirror 64, which can have curvature or may be flat. Mirror 64 is highly reflective at 106.

The intracavity infrared beam propagates to mirror 68, which is a coated mirror that is highly transmissive in the green, and highly reflective at 1.064 microns. The beam then passes through a lens 72 which focuses the intracavity infrared beam tightly into LBO crystal 36. Again, LBO 36 is positioned on a heater 38, creating a high power density inside the LBO crystal. The LBO or other doubling crystal is typically wedged and/or titled to prevent undesired feedback of any beams reflected from its surfaces. This is preferred for amplitude stable, infra-cavity doubling. The infrared beam, with a very small waist, passes through LBO crystal 36 and then strikes mirror 70, which is a dual reflector highly reflective at 532 nm and 1.064 microns. The infrared beam is then passed in a right direction back where it came from, thus creating a laser cavity. It also reflects back the green that was generated upon the first pass through LBO crystal 36. The green is then passed through lens 72 and out of the cavity through an output coupler 68 into output beam 42. Output beam 42 can be about 6 watts, 5 watts, 4 watts, 2 watts or 1 watt. FIG. 5 illustrates a double pass configurations with infrared beam passing left through LBO crystal 36 and right, resulting in the generation of green. Mirror 70 reflects the left going green and then the right going green, with both of them exiting from resonator 44 as beam 42.

Figure 6:
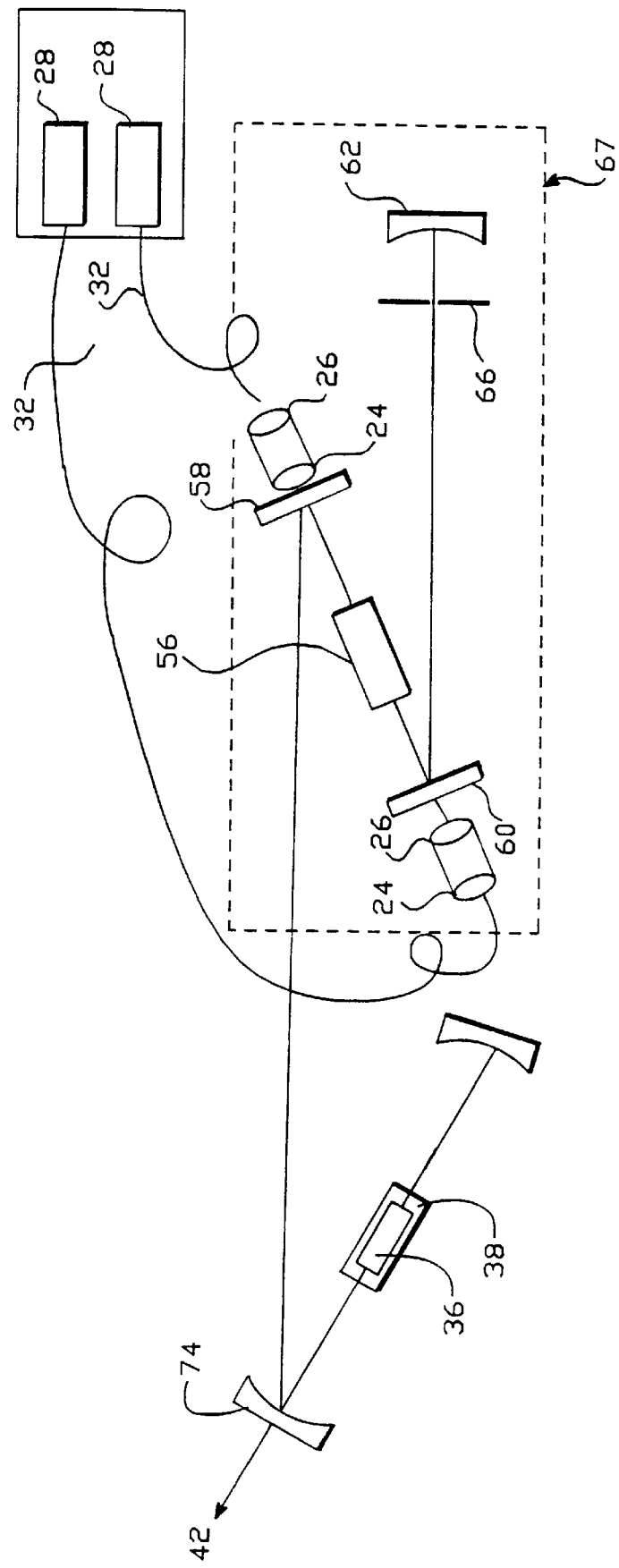
FIG. 6 is a schematic diagram of a two port, diode-pumped, multiaxial mode, intracavity-frequency-doubled laser that utilizes Nd:YVO$_4$ and LBO but uses less mirrors and optical elements than does the laser in FIG. 5.

Referring now to FIG. 6, a schematic diagram of a two port, diode-pumped, multi axial-mode, intracavity frequency doubled laser utilizing Nd:YVO$_4$ and LBO is illustrated. The laser at FIG. 6 can be, (i) shorter than the resonator in FIG. 5, for example, approximately 0.6 meters, and (ii) is simpler. It has one less mirror and one less lens. Lens 72 and mirror 64 of FIG. 5 are not included in FIG. 6. Output beam 42 is directed in a different direction through output coupler 74. Output coupler 74 has a fairly strong curvature, is highly transmissive of green, and highly reflective of infrared. Again as in FIG. 5, mirrors 58, 60 and 62 can be incorporated into a separated infrared module 67.

Nonlinear crystal KTP 36 can be also be used effectively with the present invention if care is taken to insure both phase matching and appropriate polarization rotation effects. Polarization rotation of the fundamental infrared beam occurs because of the birefringence of KTP; with the KTP acting as a multiple order waveplate, as is well known in the art. These effects must be controlled for efficient, stable, intracavity doubling when KTP is used; see for example Nightingale et al. or Weichmann et al. This is accomplished by rotating the KTP crystal to an orientation for optimal Type II doubling, angle-tuning for maximum frequency conversion, and temperature-controlling KTP crystal 36 for a single or double pass polarization rotation that matches an eigenmode of the laser cavity with a defined polarization rotation that matches an eigenmode of the laser cavity with a defined polarization state. For example, if an eigenmode has a defined polarization state within the laser crystal medium, the single or double pass of the KTP crystal and other intracavity elements should be arranged to provide the same polarization state upon one round trip of the laser cavity. One case is where the polarization is linear (i.e., vertical or horizontal) in the gain medium; other polarization states can also be used, as described by Oka et al.

These same techniques apply to the multiaxial mode case, but the use of the highly multiaxial mode doubling technique to generate amplitude stable output has not been presented by others. In an embodiment of the present invention, using Nd:YVO$_4$ pumped by 26 W of diode pump power from two fiber-coupled diode bars and a resonator configuration similar to that of FIGS. 5 and 6, approximately 5 W of TEM$_{00}$ output is generated with approximately 0.5% RMS noise.

Figure 7:
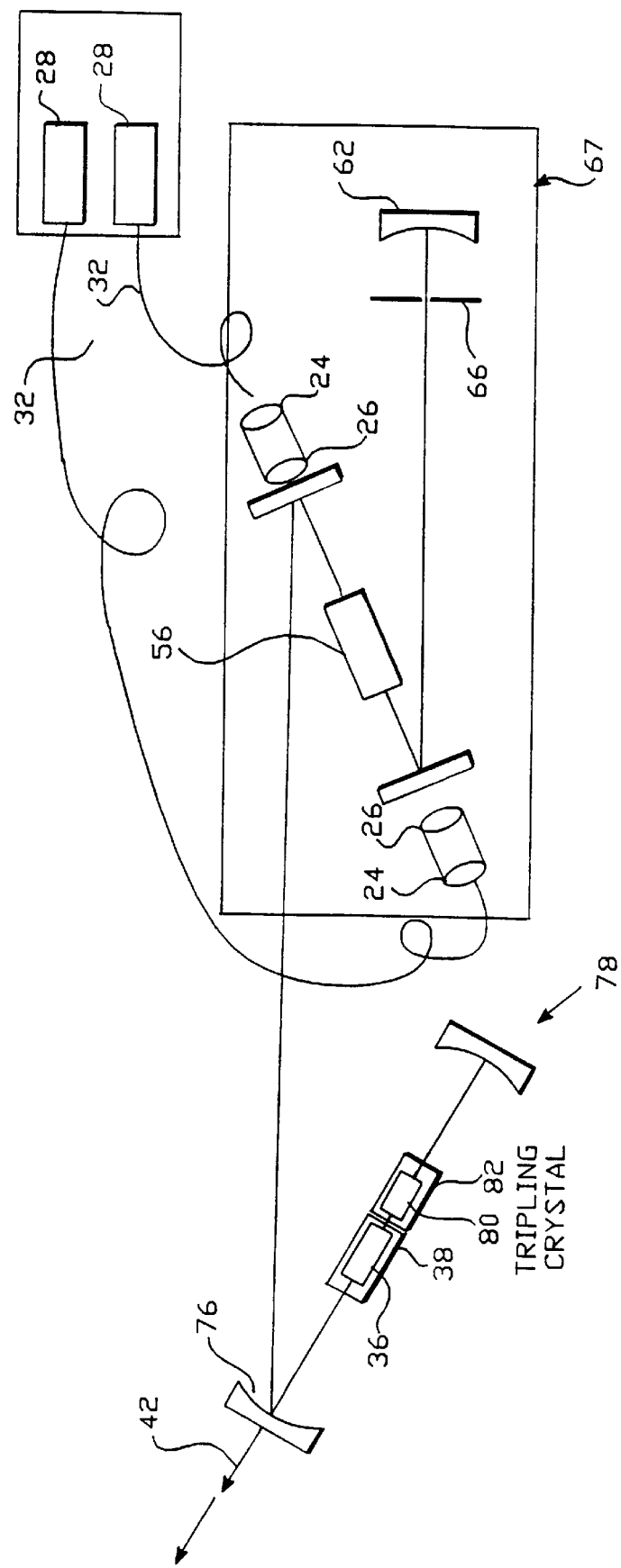
FIG. 7 is a schematic diagram of a two port, diode pumped, multiaxial mode, intracavity frequency doubled laser that utilizes Nd:YVO$_4$ and LBO, further including a frequency tripling crystal.

FIG. 7 is a schematic diagram of a two-port, diode-pumped, multi axial-mode, intracavity frequency doubled laser utilizing Nd:YVO$_4$ and LBO, and further includes a frequency tripling crystal 80. Tripling crystal 80 is mounted on a heater 82, and is positioned closely adjacent to LBO crystal 36. Mirror 76 is trichroic and highly reflective at 1.064 microns, highly transmissive at 532 nm and 355 nm. Opposing mirror 78 is a three-wavelength high reflector, e.g., it is a high reflector at 1.064 microns, highly reflective at 532 nm and at 55 nm. With the embodiment of FIG. 7, output beam 42 is a UV beam. In other configurations, two or more UV beams can be generated. It will be appreciated that tripling crystal 80 can be LBO but may also be a different material. Crystal 80 is cut at a different angle from that of LBO crystal 36 in order to achieve phase matching of a different type. That is, it does not phase match the doubling of 1064 to 532 nm. Instead, it phase matches the summation of 1064 nm and 532 nm in order to optimally generate a UV beam at 355 nm. LBO crystal 36 and crystal 80 are positioned in a close proximate relationship because this is where the mode is the smallest. It is desirable to generate high intensity both in the green and in the infrared in order to enhance the nonlinear tripling process.

Figure 8:
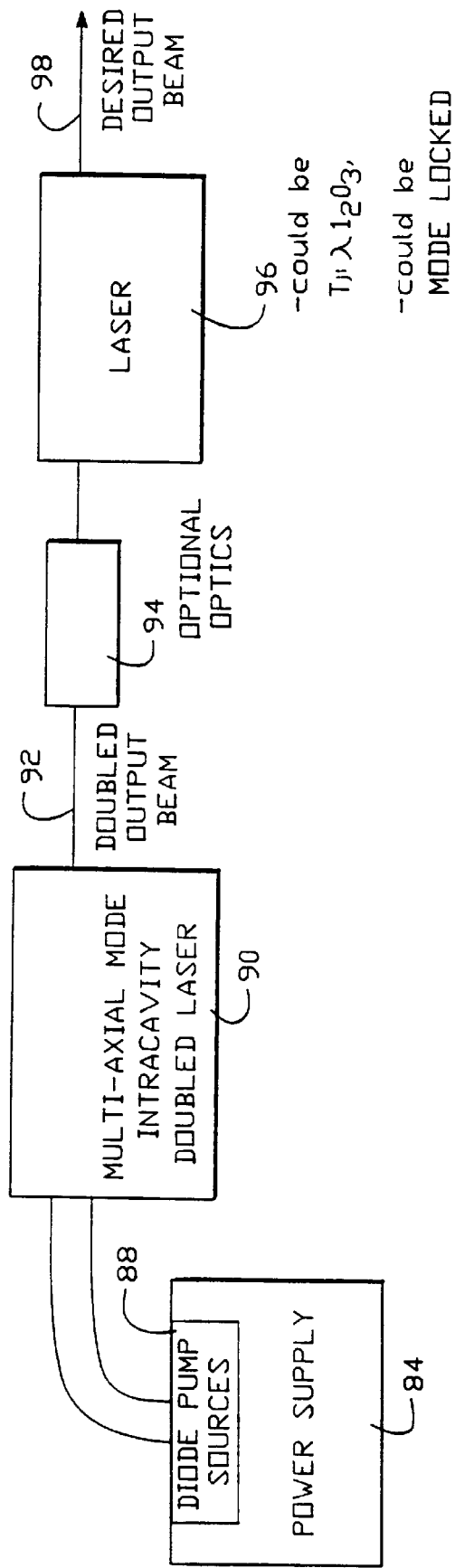
FIG. 8 is a schematic diagram of a diode pumped multi axial mode, intracavity frequency doubled laser used as a pump source for another laser, such as a Ti:Al$_2$O$_3$.

Referring now to FIG. 8, a multi-axial mode, intracavity doubled laser is used as a pump for a second laser, including but not limited to a Ti:Al$_2$O$_3$ laser. The laser illustrated in FIG. 8 includes a power supply 84, diode pump sources 88, a multi-axial mode intracavity doubled laser 90, a doubled output beam 92, optional optics 94, a second laser 96 that produces a desired output beam 98.

Referring now to FIG. 9, a retinal photocoagulator system includes a power supply and system controller 100, a power supply 102, diode pump sources 104, a multi axial mode intracavity doubled laser 106, optics 108, a beam delivery device 110, including but not limited to a fiber optic, additional optics 112, a magnifier/optical system 114 for the physician, a slit lamp 116, as well as other optical components such as mirrors.

The present invention is a diode pumped, multi axial mode, intracavity doubled laser with low amplitude noise. This is created by oscillating a plurality of axial modes, such as 10, and in some instances ~100. In one embodiment, a long resonator structure creates the multi axial modes. The length of the resonator can be in the range of 0.3 m to 2 m. Other techniques can also be used to insure multiaxial mode operation. For example the laser crystal 22 can be positioned as close as possible to one end of the resonator, taking advantage of the effects of spatial hole burning which is maximized as laser crystal 22 is moved close to an end. Additionally, a high reflecting coating can be place on laser crystal 22. Laser crystal 22 materials with broad band widths, on the order of a few hundreds of GHz, can also be used to generate the many axial modes.

Although a green output beam has been described, blue, red, near infrared and beams of other wavelengths are possible, depending on the choice of laser and doubling crystals.

Changes and modifications in the specifically described embodiments can be carried out without departing from the scope of the invention which is intended to be limited only by the scope of the appended claims.

What is claimed is:

1. A retinal photocoagulator system, comprising:

a diode-pumped multiaxial mode intracavity-doubled laser with a doubled output beam of % RMS noise of less than 10%;

a pump source optically coupled to the diode-pumped multiaxial mode intracavity-doubled laser;

a power supply coupled to the pump source; and a beam delivery device coupled to the diode-pumped multiaxial mode intracavity-doubled laser configured to supply at least a portion of the output beam to a patient's retina, the beam delivery device including a slit lamp.

2. The retinal photocoagulator system of claim 1, wherein the beam delivery device includes a magnification apparatus permitting visualization by the physician.

3. The retinal photocoagulator system of claim 2, wherein the diode-pumped multiaxial mode intracavity-doubled laser is configured such that the % RMS noise is less than 5%.

4. The retinal photocoagulator system of claim 1, wherein, the diode-pumped multiaxial mode intracavity-doubled laser is configured such that the % RMS noise is less than 5%.

5. The retinal photocoagulator system of claim 1, wherein the beam delivery device includes a magnification apparatus permitting visualization by the physician.

6. The retinal photocoagulator system of claim 5, wherein the diode-pumped multiaxial mode intracavity-doubled laser is configured such that the % RMS noise is less than 5%.

7. The retinal photocoagulator system of claim 1, wherein the diode-pumped multiaxial mode intracavity-doubled laser is configured such that the % RMS noise is less than 5%.

* * * * *